United States Patent [19]

Iwao et al.

[11] Patent Number: 4,786,635

[45] Date of Patent: Nov. 22, 1988

[54] NOVEL BENZOTHIAZINE DERIVATIVES

[75] Inventors: Jun-ichi Iwao, Takarazuka; Tadashi Iso, Sakai; Masayuki Oya, Ibaraki, all of Japan

[73] Assignee: Santen Pharmaceutical Co., Ltd., Osaka, Japan

[21] Appl. No.: 34,164

[22] PCT Filed: Jul. 21, 1986

[86] PCT No.: PCT/JP86/00379

§ 371 Date: Mar. 10, 1987

§ 102(e) Date: Mar. 10, 1987

[87] PCT Pub. No.: WO87/00838

PCT Pub. Date: Feb. 12, 1987

[30] Foreign Application Priority Data

Jul. 29, 1985 [WO] PCT Int'l Appl. ... PCT/JP85/00426
Aug. 6, 1985 [JP] Japan ............... 60-173531

[51] Int. Cl.[4] ................ A61K 31/54; C07D 279/10
[52] U.S. Cl. ............................. 514/224.2; 544/52
[58] Field of Search ........................ 544/52; 514/225

[56] References Cited

U.S. PATENT DOCUMENTS 4,584,300 4/1986 Iwao et al. ................. 514/225
4,595,685 6/1986 Henning et al. ............. 544/52

OTHER PUBLICATIONS

Morrison and Boyd, Organic Chemistry, 1978, pp. 555 and 742.
Chemische Berichte 30, pp. 809-813.

Primary Examiner—Mary C. Lee
Assistant Examiner—Zinna Northington
Attorney, Agent, or Firm—Frishauf, Holtz, Goodman & Woodward

[57] ABSTRACT

This invention relates to novel benzothizine derivatives of the formula [I], processes for preparing them and therapeutic agents for circulatory diseases containing them as an active ingredient,

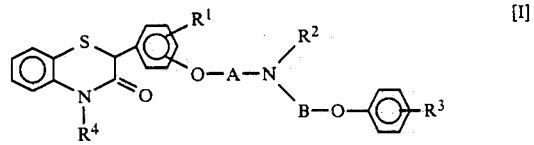

wherein $R^1$ is one or more groups selected from those consisting of hydrogen, lower alkyl, halogen, nitro, hydroxy, lower alkoxy, lower alkanoyloxy, amino, lower alkylamino and lower alkoxycarbonyloxy;

$R^2$ is hydrogen, lower alkyl or ($C_3$-$C_6$)cycloalkyl;

$R^3$ is one or more groups selected from those consisting of hydrogen, lower alkyl, hydroxy, lower alkoxy, halogen, nitro, lower alkylenedioxy, lower alkanoyloxy, lower alkanoyl, amino, lower alkylamino, lower alkanoylamino and lower alkoxycarbonyloxy or $(CH_2)_n$;

$R^4$ is hydrogen or lower alkyl.

17 Claims, No Drawings

NOVEL BENZOTHIAZINE DERIVATIVES

FIELD OF THE ART

This invention relates to benzothiazine derivatives which possess anti-platelet aggregation and calcium antagonism effects and are useful for treatment of circulatory diseases.

BACKGROUND OF THE INVENTION

There were few studies on benzothiazine derivatives useful as therapeutic drugs. Especially, there is only one prior publication, Japanese Unexamined Patent Publication No. 148771/84 filed by the same inventors of this invention, disclosing the compounds useful for treatment of circulatory diseases of the present object. The inventors further advanced the previous study to find out novel and useful compounds. The characteristic of the chemical structure of the compounds of this invention is that phenyl group substituted at 2-position of benzothiazine ring has a side chain which has a substituted or unsubstituted phenyloxy group. Such structural characteristic has not been disclosed in the above Japanese Unexamined Patent Publication No. 148771/84.

As other prior arts concerning compounds having benzothiazine ring, there exists publications by J. Krapcho (U.S. Pat. No. 3166554), Stearns et al. (U.S. Pat. No. 3,555,155) and Stanley O. et al. (Can. Pat. No. 717979). The chemical structures of the compounds disclosed in the respective patents are different from those of this invention and the objects thereof are also different. The object of the patent of J. Krapcho is a treatment of Parkinsonism, the patent of Stearns et al. is on herbicides, and the patent of Stanley et al. is on medicines having anticholinergic activity and antihistaminic activity.

The object of this invention is to search and find more useful drugs for circulatory diseases based on the prior arts.

DISCLOSURE OF THE INVENTION

This invention relates to benzothiazine derivatives of the formula [I] and salts thereof, processes for preparing them and therapeutic drugs for circulatory diseases containing either of them as an active ingredient,

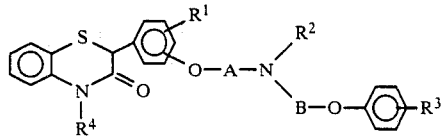

[I]

wherein
$R^1$ is one or more groups selected from those consisting of hydrogen, lower alkyl, halogen, nitro, hydroxy, lower alkoxy, lower alkanoyloxy, amino, lower alkylamino and lower alkoxycarbonyloxy;
$R^2$ is hydrogen, lower alkyl or $(C_3-C_6)$cycloalkyl;
$R^3$ is one or more groups selected from those consisting of hydrogen, lower alkyl, hydroxy, lower alkoxy, halogen, nitro, lower alkylenedioxy, lower alkanoyloxy, lower alkanoyl, amino, lower alkylamino, lower alkanoylamino and lower alkoxycarbonyloxy or

$R^4$ is hydrogen or lower alkyl;
A and B are the same or different and are lower alkylene having 1 to 6 carbon atoms; and
n is 3 to 4.
The same shall be applied hereinafter.

The groups defined above are explained below more in detail:

Lower alkyl is an alkyl group having 1 to 6 carbon atoms exemplified by methyl, ethyl, propyl and hexyl; halogen is exemplified by fluorine, chlorine and bromine; lower alkoxy is an alkoxy group having 1 to 6 carbon atoms exemplified by methoxy, ethoxy, propoxy and hexyloxy; lower alkanoyloxy is an alkanoyloxy group having 1 to 6 carbon atoms exemplified by acetyloxy, propionyloxy and hexanoyloxy; $(C_3-C_6)$ cycloalkyl is a cycloalkyl group having 3 to 6 carbon atoms exemplified by cyclopropyl and cyclohexyl; lower alkylenedioxy is a group which have $(C_1-C_6)$ alkylene between two oxygen atoms exemplified by methylenedioxy and ethylenedioxy; lower alkanoyl is an alkanoyl group having 1 to 6 carbon atoms exemplified by acetyl, propionyl and hexanoyl.

The compounds of this invention can be prepared by the following methods.

(1) A reaction of a compound of the formula [II] with amine derivative of the formula [III] under basic conditions.

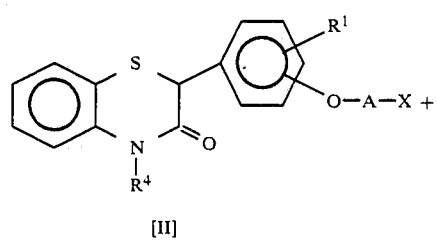

[II]

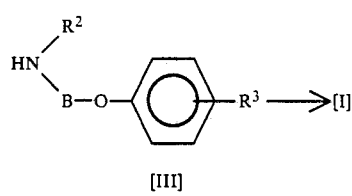

[III]

wherein X is halogen or methanesulfonyloxy. The same shall be applied hereinafter.

(2) A reaction of a compound of the formula [IV] with a compound of the formula [V].

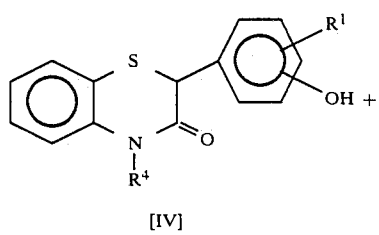

[IV]

-continued

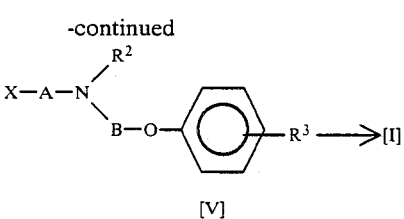

[V]

(3) A reaction of a compound of the formula [VI] with a compound of the formula [VII]:

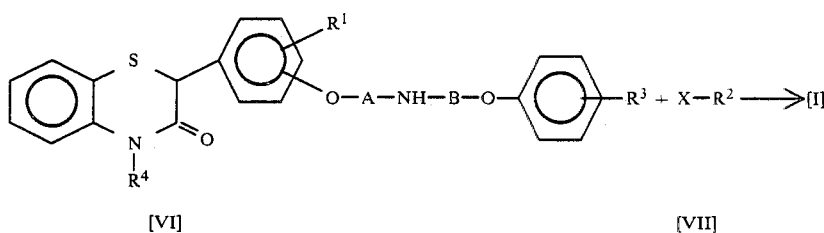

The above reactions are usually carried out under basic conditions. Examples of a preferable base is inorganic or organic base such as sodium hydride, potassium carbonate, sodium carbonate, sodium hydroxide, sodium alcholate, triethylamine, pyridine or N,N-dimethylaniline. The reactions can be carried out using an excess amount of amine reactant without adding a base.

The compounds of this invention have stereoisomers, and such isomers are included in the scope of this invention.

Optically active compounds of the formula [I] can be obtained from racemic compounds of the formula [I] by the known methods such as optical resolution method using optical active organic acid exemplified by mandelic acid and separation method using cellulose triacetate column as a separator.

Optically active compounds of the formula [I] can be also prepared by using an optically active starting material in the processes for preparing the compounds of the formula [I]. An example for preparing an optically active starting material is shown below.

[IV], the optically active compounds of the formula [I] can be prepared.

The conditions such as solvent and reaction temperature are not necessarily limited and can be selected depending on a kind of base, solubility of a reactant, etc.

The compounds of this invention can be converted into pharmaceutically acceptable salts. Examples of the salts are hydrochloride acid salt, sulfuric acid salt, phosphoric acid salt, lactic acid salt, maleic acid salt, fumaric acid salt, oxalic acid salt, methanesulfonic acid salt and p-toluenesulfonic acid salt.

The compounds of this invention can be administered either orally or parenterally. Examples of the dosage forms are tablet, capsule, granule, powder, suppository, injection, etc. The dosage is adjusted depending on symptom, dosage form, etc., but usual daily dosage is 1 to 5,000 mg, preferably 10 to 1,000 mg, in one or a few divided doses.

The compounds of this invention have platelet antiagrregation activity and calcium-antagonism activity, and they are useful for treatment of circulatory diseases such as hypertension, thrombosis and arrhythmia.

As the pharmacological test to prove the effects of the compounds of this invention, a test on calcium-antagonism activity is shown as follows.

As typical compounds of this invention, 3,4-dihydro-2-[5-methoxy-2-[4-[N-methyl-N-[2-[(3,4-methylenedioxy)phenoxy]ethyl]amino]butoxy]phenyl]-4-methyl-3-oxo-2H-1,4-benzothiazine oxalate (defined as Compound A for short hereinafter), 3,4-dihydro-2-[5-methoxy-2-[3-[N-methyl-N-[2-[(3,4-methylenedioxy)-phenoxy]ethyl]amino]propoxy]phenyl]-4-methyl-3-

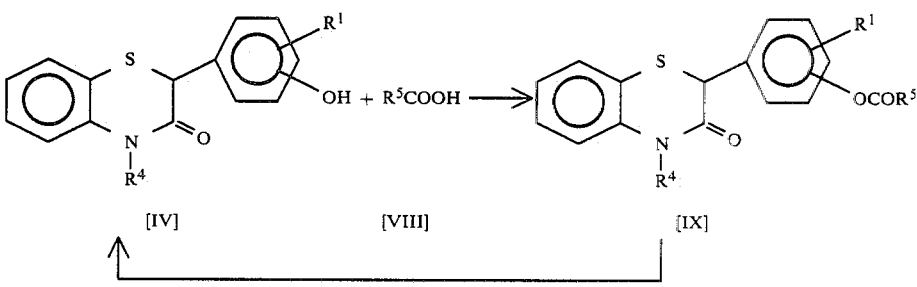

wherein $R^5$ is a residual group of carboxylic acid derivatives having one or more asymmetric carbon atoms.

A mixture of diastereomers of the formula [IX] is prepared by a reaction of a racemic compound of the formula [IV] with carboxylic acid of the formula [VIII] having an assymetric carbon atom using a condensing agent such as DCC. The mixture of diastereomers is separated and followed by removal of $R^5$CO-group by a method such as hydrolysis and reduction to give the desired optically active compound of the formula [IV]. Using the optically active compound of the formula oxo-2H-1,4-benzothiazine fumarate (defined as Compound B for short hereinafter) and 3,4-dihydro-2-[5-methoxy-2-[4-[N-methyl-N-[2-[(3,4-dimethoxy)phenoxy]ethyl]amino]butoxy]phenyl]-4-methyl-3-oxo-2H-1,4-benzothiazine oxalate (defined as Compound C for short hereinafter) were tested.

As a reference compound, 3,4-dihydro-2-[5-methoxy-2-[4-[N-methyl-(3,4-dimethoxy)phenetylamino]butoxy]phenyl]-4-methyl-3-oxo-2H-1,4-benzothiazine oxalate (mp 145°-147° C.) was used. The structure of the reference compound resembles to the compound of this invention. But, it has not characteristic structure of the compound of this invention that is a existence of a phenyloxy group in the side chain.

Pharmacological Test (Method for mesurement of calcium-antagonistic activity)

Isolated guinea-pig taenia coli was suspended in a 20 ml organ bath filled with Krebs solution at 32° C. and bubbled with 5% carbon dioxide in oxygen. After equilibration, the muscle was suspended in $Ca^{++}$-free Krebs solution. The muscle was then exposed to the test compound for 5 minutes before the addition of $CaCl_2$, and the contraction induced by $CaCl_2 (3 \times 10^{-4}M)$ was recorded isotonically. The calcium-antagonistic activity was represented by the concentration of the test compound which elicited 50% inhibition ($IC_{50}$) of $Ca^{++}$-induced contraction.

(Result)

| Compound | $IC_{50}$ (M) |
| --- | --- |
| Compound A | $3.2 \times 10^{-7}$ |
| Compound B | $2.4 \times 10^{-7}$ |
| Compound C | $2.9 \times 10^{-7}$ |
| Reference Compound | $3.2 \times 10^{-6}$ |

BEST MODE TO MAKE THE INVENTION

Example 1

3,4-Dihydro-2-[5-methoxy-2-[4-[N-methyl-N-[2-[(3,4-methylenedioxy)phenoxy]ethyl]amino]butoxy]phenyl]-4-methyl-3-oxo-2H-1,4-benzothiazine oxalate To a suspension of 50% sodium hydride (0.15 g) in anhydrous dimethylformamide (5 ml), a solution of 3,4-dihydro-2-(2-hydroxy-5-methoxyphenyl)-3-oxo-2H-1,4-benzothiazine (0.9 g) in anhydrous dimethylformamide (10 ml) was added dropwise with stirring. After the addition, the mixture was stirred additionally for 15 minutes. To the mixture, a solution of 4-[N-methyl-N-[2-[(3,4-methylenedioxy)phenoxy]ethyl]amino]butoxy bromide (1.2 g) in anhydrous dimethylformamide (10 ml) was added dropwise with stirring. The mixture was then stirred for 2 hours at 50° C. The reaction mixture was poured into a mixture of chloroform (50 ml) and 2N hydrochloric acid (50 ml).

The organic layer was concentrated in vacuo and the residue was dissolved in ethyl acetate. The solution was washed with N sodium hydroxide and then with saturated sodium chloride solution.

The organic layer was dried over anhydrous sodium sulfate and concentrated in vacuo. The resulting residue was purified by a silica gel column chromatography and the oily product was dissolved in ethyl acetate. To this solution, a solution of oxalic acid in ethyl acetate was added and the resulting crystals were filtered to give 1.4 g (73%) of the titled compound.

mp 160°–162° C. (ethanol-water).

IR (KBr, cm$^{-1}$, the same shall be applied hereinafter unless specified): 1655, 1584, 1499, 1475, 1400, 1356, 1277, 1238, 1205, 1185, 1132, 1034.

The following compounds were prepared by the similar method as in Example 1.

3,4-Dihydro-2-[5-methoxy-2-[3-[N-methyl-N-[2-[(3,4-methylenedioxy)phenoxy]ethyl]amino]propoxy]-phenyl]-4-methyl-3-oxo-2H-1,4-benzothiazine fumarate:

mp 130°–131° C. (ethanol).
IR: 1654, 1473, 1239, 1209, 1183, 1033.
hydrochloride:
mp 133°–134.5° C. (ethanol).
IR: 2416, 1654, 1478, 1236, 1182, 1034.

3,4-Dihydro-2-[2-[4-[N-[2-(4-methoxyphenoxy)ethyl]-N-methylamino]butoxy]-5-methoxyphenyl]-4-methyl-3-oxo-2H-1,4-benzothiazine oxalate mp 149°–150° C. (ethanol—water).
IR: 1674, 1473, 1238, 1218, 1037.

3,4-Dihydro-2-[5-methoxy-2-[3-[N-methyl-N-[2-[(3,4,5-trimethoxy)phenoxy]ethyl]amino]propoxy]phenyl]-4-methyl-3-oxo-2H-1,4-benzothiazine oxalate mp 137°–139° C. (ethanol—ethyl acetate).
IR: 1715, 1653, 1589, 1489, 1457.

3,4-Dihydro-2-[4-[3-[N-methyl-N-[2-[(3,4-methylenedioxy)phenoxy]ethyl]amino]propoxy]phenyl]-4-methyl-3-oxo-2H-1,4-benzothiazine oxalate mp 146°–148° C. (ethanol).
IR: 1648, 1582, 1473, 1399, 1356.

3,4-Dihydro-2-[4-[2-[N-methyl-N-[2-[(3,4-methylenedioxy)phenoxy]ethyl]amino]ethoxy]phenyl]-4-methyl-3-oxo-2H-1,4-benzothiazine oxalate mp 97°–102° C. (acetone).
IR: 1647, 1478, 1398, 1237, 1182.

3,4-Dihydro-2-[5-methoxy-2-[2-[N-methyl-N-[2-[(3,4-methylenedioxy)phenoxy]ethyl]amino]ethoxy]phenyl]-4-methyl-3-oxo-2H-1,4-benzothiazine oxolate mp 129°–131.5° C. (ethyl acetate—methanol).
IR: 1645, 1474, 1399, 1236, 1183.

3,4-Dihydro-2-[5-methoxy-2-[4-[N-methyl-N-[2-[(3,4-dimethoxy)phenoxy]ethyl]amino]butoxy]phenyl]-3-oxo-2H-1,4-benzothiazine hydrochloride

IR: 1653 (C=O).

2-[4-[4-[N-[2-(2-chlorophenoxy)ethyl]-N-ethylamino]-butoxy]phenyl]-3,4-dihydro-4-methyl-3-oxo-2H-1,4-benzothiazine hydrochloride

IR: 1655 (C=O).

3,4-Dihydro-2-[5-methoxy-2-[4-[N-methyl-N-[2-[(3,4-methylenedioxy)phenoxy]methylamino]butoxy]phenyl-4-methyl-3-oxo-2H-1,4-benzothiazine oxalate

IR: 1654 (C=O).

Example 2

3,4-Dihydro-2-[5-methoxy-2-[3-[N-methyl-N-[2-[(3,4-methylenedioxy)phenoxy]ethyl]amino]propoxy]-phenyl]-4-methyl-3-oxo-2H-1,4-benzothiazine fumarate To a stirred solution of 2-[2-(3-bromopropoxy)-5-methoxyphenyl]-3,4-dihydro-4-methyl-3-oxo-2H-1,4-benzothiazine (1.2 g) and sodium carbonate (0.4 g) in dimethylformamide (5 ml), N-methyl-2-[(3,4-methylenedioxy)phenoxy]ethylamine (0.8 g) was added and the mixture was stirred for 2 hours at 80° C. The reaction mixture was poured into a mixture of chloroform (50 ml) and 2N hydrochloric acid (50 ml). The following treatments were carried out by the similar procedure as in Example 1 to give 1.3 g (70%) of the titled compound.

mp 130°–131° C. (ethanol).

IR: 1654, 1473, 1239, 1209, 1183, 1033.

The following compounds were prepared by the similar method as in Example 2.

3,4-Dihydro-2-[2-[4-[N-[2-[(2,6-dimethoxy)phenoxy]ethyl-N-methyl]amino]butoxy]-5-methoxyphenyl]-4-methyl-3-oxo-2H-1,4-benzothiazine hydrochloride

IR: 1652, 1473, 1238, 1207, 1104.

3,4-Dihydro-2-[5-chloro-2-[3-[N-methyl-N-[2-[(3,4-methylenedioxy)phenoxy]ethyl]amino]propoxy]phenyl]-4-methyl-3-oxo-2H-1,4-benzothiazine fumarate mp 116°–118° C. (ethanol).
IR: 1654, 1474, 1357, 1265, 1240.

3,4-Dihydro-2-[2-[4-[N-[2-[(5-indanyloxy)ethyl]-N-methylamino]butoxy]-5-methoxyphenyl]-4-methyl-3-oxo-2H-1,4-benzothiazine oxalate mp 145°–146° C. (ethanol—water).
IR: 1673, 1474, 1239, 1217.

3,4-Dihydro-2-[4-[4-[N-methyl-N-[2-[(3,4-methylenedioxy)phenoxy]ethyl]amino]butoxy]phenyl]-4-methyl-3-oxo-2H-1,4-benzothiazine oxalate mp 105°–108° C. (ethanol).
IR: 1646, 1582, 1476, 1399, 1357.

3,4-Dihydro-2-[5-methoxy-2-[4-[N-methyl-N-[2-(phenoxy)ethyl]amino]butoxy]phenyl]-4-methyl-3-oxo-2H-1,4-benzothiazine oxalate

IR: 1655 (C=O).

3,4-Dihydro-2-[5-methoxy-2-[5-[N-methyl-N-[2-(3,4,5-trimethoxy)phenoxy]ethyl]amino]pentyloxy]phenyl]-4-methyl-3-oxo-2H-1,4-benzothiazine oxalate

IR: 1655 (C=O).

3,4-Dihydro-2-[5-methoxy-2-[4-[N-methyl-N-[2-(3,4-methylenedioxy)phenoxy]ethyl]amino]butoxy]phenyl]-3-oxo-2H-1,4-benzothiazine hydrochloride

IR: 1655 (C=O).

3,4-Dihydro-2-[5-chloro-2-[3-[N-methyl-N-[2-(3,4-dimethoxy)phenoxy]ethyl]amino]propoxy]phenyl]-4-methyl-3-oxo-2H-1,4-benzothiazine hydrochloride

IR: 1655 (C=O).

3,4-Dihydro-2-[5-methoxy-2-[3-[N-methyl-N-[2-(4-methoxyphenoxy)ethyl]amino]propoxy]phenyl]-3-oxo-2H-1,4-benzothiazine fumarate

IR: 1656 (C=O).

3,4-Dihydro-2-[2-[3-[N-[2-(2-fluorophenoxy)ethyl-N-methyl]amino]propoxy]-5-methoxyphenyl]-4-methyl-3-oxo-2H-1,4-benzothiazine hydrochloride

IR: 1656 (C=O).

2-[4-[4-[N-Cyclopropyl-N-[2-(4-nitrophenoxy)ethyl]amino]butoxy]phenyl]-3,4-dihydro-4-methyl-3-oxo-2H-1,4-benzothiazine oxalate

IR: 1656 (C=O).

3,4-Dihydro-2-[5-methoxy-2-[3-[N-methyl-N-[2-[(3,4-dimethoxy)phenoxy]ethyl]amino]propoxy]-4-nitrophenyl]-4-methyl-3-oxo-2H-1,4-benzothiazine oxalate

IR: 1654 (C=O).

3,4-Dihydro-2-[2-[4-[N-ethyl-N-[2-[(2,3,4-trimethoxy)phenoxy]ethyl]amino]butoxy]-4-methoxyphenyl]-4-methyl-3-oxo-2H-1,4-benzothiazine oxalate

IR: 1653 (C=O).

3,4-Dihydro-2-[5-methoxy-N-[2-[3-[2-[(3,4-methylenedioxy)phenoxy]ethyl]amino]propoxy]phenyl]-4-methyl-3-oxo-2H-1,4-benzothiazine hydrochloride

IR: 1656 (C=O).

3,4-Dihydro-2-[2-[4-[N-[2-(4-chlorophenoxy)ethyl]-N-cyclohexylamino]butoxy]-5-methoxyphenyl]-4-methyl-3-oxo-2H-1,4-benzothiazine oxalate

IR: 1655 (C=O).

3,4-Dihydro-4-methyl-2-[4-[3-[N-[2-[(3,4,5-trimethoxy)phenoxy]ethyl]amino]propoxy]phenyl]-3-oxo-2H-1,4-benzothiazine hydrochloride

IR: 1657 (C=O).

3,4-Dihydro-2-[4-[5-[N-cyclohexyl-N-[2-[(4-methylphenoxy)ethyl]amino]pentyloxy]phenyl]-4-methyl-3-oxo-2H-1,4-benzothiazine hydrochloride

IR: 1658 (C=O).

3,4-Dihydro-2-[4-[5-[N-methyl-N-[(2,3,4-trimethoxy)phenoxy]methylamino]pentyloxy]phenyl]-4-methyl-3-oxo-2H-1,4-benzothiazine hydrochloride

IR: 1655 (C=O).

Example 3

3,4-Dihydro-2-[5-methoxy-2-[3-[N-methyl-N-[2-[(3,4-methylenedioxy)phenoxy]ethyl]amino]propoxy]phenyl]-4-methyl-3-oxo-2H-1,4-benzothiazine fumarate To a solution of 3,4-dihydro-2-[5-methoxy-2-[3-(methylamino)propoxy]phenyl]-4-methyl-3-oxo-2H-1,4-benzothiazine (1.2 g) and triethylamine (0.4 g) in ethanol (10 ml), 2-[(3,4-methylenedioxy)phenoxy]ethyl methanesulfonate (1.0 g) was added and the mixture was refluxed for 2 hours. The reaction mixture was concentrated in vacuo and the residue was poured into a mixture of chloroform (50 ml) and 2N hydrochloric acid (50 ml). The following treatments were carried out by the similar procedures in Example 1 to give 1.3 (65%) of the titled compound. The melting point and IR data of the compound were identical with the crystals prepared in Example 2.

The following compounds were prepared by the similar method as in Example 3.

3,4-Dihydro-2-[2-[4-[N-[2-[(3,4-dimethoxy)phenoxy]ethyl-N-methyl]amino]butoxy]-5-methoxyphenyl]-4-methyl-3-oxo-2H-1,4-benzothiazine oxalate mp 167°–168° C. (ethanol—water).
IR: 1653, 1500, 1458, 1217, 1198.

3,4-Dihydro-2-[5-methyl-2-[3-[N-methyl-N-[2-[(3,4-methylenedioxy)phenoxy]ethyl]amino]propoxy]phenyl]-4-methyl-3-oxo-2H-1,4-benzothiazine fumarate mp 114°–116° C. (ethanol).
IR: 1652, 1582, 1466, 1355, 1304.

3,4-Dihydro-2-[4-[3-[N-2-[(5-indanyloxy)ethyl-N-methyl]amino]propoxy]-5-methoxyphenyl]-4-methyl-3-oxo-2H-1,4-benzothiazine oxalate mp 107°–109° C. (ethyl acetate).
IR: 1661, 1472, 1240, 1214, 1041.

3,4-Dihydro-2-[5-methoxy-2-[2-[N-methyl-N-[3-[(3,4-methylenedioxy)phenoxy]propyl]amino]ethoxy]-phenyl]-4-methyl-3-oxo-2H-1,4-benzothiazine oxalate mp 121°–126° C. (ethanol).
IR: 1627, 1464, 1354, 1276, 1181.

3,4-Dihydro-4-methyl-2-[4-[4-[N-methyl-N-[2-[(3,4-methylenedioxy)phenoxy]ethyl]amino]butoxy]phenyl]-3-oxo-2H-1,4-benzothiazine oxalate

IR: 1654 (C=O).

3,4-Dihydro-2-[4-[4-[N-[2-(2-fluorophenoxy)ethyl]amino]butoxy]phenyl]-4-methyl-3-oxo-2H-1,4-benzothiazine hydrochloride

IR: 1660 (C=O).

3,4-Dihydro-2-[4-[4-[N-methyl-N-[2-(2-chlorophenoxy)ethyl]amino]butoxy]phenyl]-3-oxo-2H-1,4-benzothiazine fumarate

IR: 1662 (C=O).

3,4-Dihydro-2-[5-methoxy-2-[3-[N-methyl-N-[(3,4-dimethoxy)phenoxy]methylamino]propoxy]phenyl]-4-methyl-3-oxo-2H-1,4-benzothiazine hydrochloride

IR: 1658 (C=O).

EXAMPLE 4

3,4-Dihydro-2-[5-methoxy-2-[4-[N-methyl-N-[2-[(3,4,5-trimethoxy)phenoxy]ethyl]amino]butoxy]phenyl]-4-methyl-3-oxo-2H-1,4-benzothiazine oxalate To a solution of 2-[2-(4-bromobutoxy)-5-methoxyphenyl]-3,4-dihydro-4-methyl-3-oxo-2H-1,4-benzothiazine (1.3 g) and triethylamine (0.4 g) in ethanol (10 ml), N-methyl-2-[(3,4,5-trimethoxy)phenoxy]ethylamine (0.9 g) was added and the mixture was refluxed for 2 hours. The reaction mixture was concentrated in vacuo and the residue was poured into a mixture of chloroform (50 ml) and 2N hydrochloric acid (50 ml). The following treatments were carried out by the similar procedures as in Example 1 to give 1.5 g (73%) of the titled compound.

mp 149°–151° C. (ethanol—water).
IR: 1653, 1591, 1499, 1458, 1234, 1217.

The following compounds were prepared by the similar method as in Example 4.

3,4-Dihydro-2-[5-methoxy-2-[3-[N-methyl-N-[2-[(2,6-dimethoxy)phenoxy]ethyl]amino]propoxy]phenyl]-4-methyl-3-oxo-2H-1,4-benzothiazine hydrochloride mp 185°–187° C. (ethanol).
IR: 1654, 1584, 1475, 1351, 1243.

3,4-Dihydro-2-[[3-[N-methyl-N-[2-[(3,4-methylenedioxy)phenoxy]ethyl]amino]propoxy]-5-nitrophenyl]-4-methyl-3-oxo-2H-1,4-benzothiazine fumarate mp 135°–137° C. (ethanol).
IR: 1654, 1584, 1477, 1388, 1260.

3,4-Dihydro-2-[5-methoxy-2-[3-[N-methyl-N-[3-[(3,4methylenedioxy)phenoxy]propyl]amino]propoxy]-phenyl]-4-methyl-3-oxo-2H-1,4-benzothiazine fumarate mp 146°–148° C. (ethanol).
IR: 1659, 1583, 1472, 1355, 1238.

3,4-Dihydro-2-[5-methoxy-2-[4-[N-methyl-N-[3-[(3,4-methylenedioxy)phenoxy]propyl]amino]butoxy]-phenyl]-4-methyl-3-oxo-2H-1,4-benzothiazine oxalate mp 135°–138° C. (ethanol).
IR: 1653, 1467, 1355, 1237.

EXAMPLE 5

Optical resolution of 3,4-dihydro-2-[5-methoxy-2-[4-[N-methyl-N-[2-[(3,4-methylenedioxy)phenoxy]ethyl]amino]butoxy]phenyl]-4-methyl-3-oxo-2H-1,4-benzothiazine by a cellulose triacetate column chromatography A solution of the racemic compound (4.0 g) dissolved in chloroform was put into a column packed with fine crystalline cellulose triacetate (750 g), which was prepared according to the method of Chromatographia, 6, 277 (1973), and eluted with 95% ethanol to give (+)-compound and (−)-compound as free forms.

The free compounds were converted into fumarates by a usual method. 1.62 Gram and 1.50 g of fumarate of (+)- and (−)-compound were obtained respectively.

fumarate of (+)-compound
mp 148.5°–149.5° C. (ethyl acetate—ethanol).
$[\alpha]_D^{25} +195.4°$ (c=1.0, dimethylsulfoxide).
IR: 3392, 2912, 1653, 1473, 1353, 1239, 1204, 1184, 1033.

fumarate of (−)-compound
mp 149°–150° C. (ethyl acetate—ethanol).
$[\alpha]_D^{25} -195.5°$ (c=1.0, dimethylsulfoxide).
IR: 3380, 2910, 1653, 1473, 1353, 1239, 1202, 1184, 1033.

The following compounds were prepared by the similar method as in Example 5.

(+)-3,4-Dihydro-2-[5-methoxy-2-[4-[N-methyl-N-[2-[(3,4,5-trimethoxy)phenoxy]ethyl]amino]butoxy]-phenyl]-4-methyl-3-oxo-2H-1,4-benzothiazine fumarate mp 133°–135° C. (ethanol).
$[\alpha]_D^{25} +177.0°$ (c=1.0, dimethylsulfoxide).
IR: 3400, 1664, 1465, 1220, 1125.

(−)-3,4-Dihydro-2-[5-methoxy-2-[4-[N-methyl-N-[2-[(3,4,5-trimethoxy)phenoxy]ethyl]amino]butoxy]-phenyl]-4-methyl-3-oxo-2H-1,4-benzothiazine fumarate mp 133°–135° C. (ethanol).
$[\alpha]_D^{25} -180.8°$ (c=1.0, dimethylsulfoxide).
IR: 3400, 1663, 1465, 1219, 1126.

(+)-3,4-Dihydro-2-[5-methoxy-2-[3-[N-methyl-N-[2-[(3,4-methylenedioxy)phenoxy]ethyl]amino]propoxy]-phenyl]-4-methyl-3-oxo-2H-1,4-benzothiazine fumarate mp 133°–133.5° C. (ethanol).
$[\alpha]_D^{25} +194.2°$ (c=1.0, dimethylsulfoxide).
IR: 1653, 1470, 1357, 1267, 1239, 1183, 1139, 1106, 1034, 980.

(−)-3,4-Dihydro-2-[5-methoxy-2-[3-[N-methyl-N-[2-[(3,4-methylenedioxy)phenoxy]ethyl]amino]propoxy]-phenyl]-4-methyl-3-oxo-2H-1,4-benzothiazine fumarate mp 133°–133.5° C. (ethanol).

$[\alpha]_D^{25}-195.5°$ (c=1.0, dimethylsulfoxide).
IR: 1653, 1466, 1357, 1267, 1239, 1183, 1139, 1106, 1033, 980.

EXAMPLE 6

Optical resolution of 3,4-dihydro-2-[5-methoxy-2-[4-[N-methyl-N-[2-[(3,4-methylenedioxy)phenoxy]ethyl]amino]butoxy]phenyl]-4-methyl-3-oxo-2H-1,4-benzothiazine by mandelic acid To a solution of the racemic compound (5.0 g) in acetone (10 ml), L-(+)-mandelic acid (0.59 g) was added and made the mixture solution. The separated crystals were collected by filtration and recrystallized with acetone to give 1.45 g of L-(+)-mandlate of (+)-compound. The filtrate was concentrated in vacuo and the residue was dissolved in ethyl acetate. The ethyl acetate solution was washed with saturated sodium bicarbonate solution, dried over anhydrous magnesium sulfate, concentrated in vacuo, and the residue was dissolved in acetone (10 ml). To the solution D-(−)-mandelic acid (0.59 g) was added and dissolved.

Precipitated crystals were collected by filtration and recrystallized with acetone to give 1.52 g of D-(−)-mandelate of (−)-compound.

L-(+)-mandelate of (+)-compound
mp 101°–102.5° C.
$[\alpha]_D^{25}+209.9°$ (c=1.0, dimethylsulfoxide).
IR: 3396, 1664, 1584, 1500, 1490, 1478, 1356, 1240, 1219, 1190, 1036, 755.

D-(−)-mandelate of (−)-compound
mp 98.5°–100° C.
$[\alpha]_D^{25}-205.9°$ (c=1.0, dimethylsulfoxide).
IR: 3392, 1663, 1583, 1500, 1487, 1477, 1355, 1239, 1218, 1188, 1035, 754.

The mandelates can be made to free forms of (+)- and (−)- compound by a usual method and then converted into fumarates.

The physical data of the fumarates were identical with the salts obtained in Example 5.

The following compounds were prepared by the similar method as in Example 6.

(+)-3,4-Dihydro-2-[5-methoxy-2-[3-[N-methyl-N-[2-[(3,4-methylenedioxy)phenoxy]ethyl]amino]propoxy]-phenyl]-4-methyl-3-oxo-2H-1,4-benzothiazne
(+)-mandelate mp 113.5°–114.5° C. (acetone).
$[\alpha]_D^{25}+205.9°$ (c=1.1, dimethylsulfoxide).
IR: 1666, 1584, 1489, 1280, 1192, 1036.

(−)-3,4-Dihydro-2-[5-methoxy-2-[3-[N-methyl-N-[2-[(3,4-methylenedioxy)phenoxy]ethyl]amino]propoxy]-phenyl]-4-methyl-3-oxo-2H-1,4-benzothiazine
(−)-mandelate mp 114°–115° C. (acetone).
$[\alpha]_D^{25}-214.1°$ (c=1.0, dimethylsulfoxide).
IR: 1664, 1583, 1488, 1280, 1191, 1035.

The mandelates can be made to free forms of (+)- and (−)- compound by a usual method and then converted into fumarates.

The physical data of the fumarates were identical with the salts obtained in Example 5.

Example 7

Synthesis of optically active 3,4-dihydro-2-[5-methoxy-2-[3-[N-methyl-N-[2-[(3,4-methylenedioxy)phenoxy]ethyl]amino]propoxy]-phenyl]-4-methyl-3-oxo-2H-1,4-benzothiazine fumarate by using optically active 3,4-dihydro-2-(2-hydroxy-5-methoxyphenyl)-4-methyl-3-oxo-2H-1,4-benzothiazine (i) To a solution of 3,4-dihydro-2-(2-hydroxy-5-methoxyphenyl)-4-methyl-3-oxo-2H-1,4-benzothiazine (24.1 g) in anhydrous dimethylformamide (100 ml), (2S,4S)-3-acetyl-5,5-dimethyl-2-(2-methoxyphenyl)-4-thiazolidinecarboxylic acid (37.1 g), 4-dimethylaminopyridine (1.95 g) and then dicyclohexylcarbodiimide (DCC) (24.8 g) dissolved in anhydrous dimethylformamide (100 ml) were added.

The mixture was stirred for 3 hours at room temperature and then filtered. To the filtrate, water (500 ml) was added and extracted with ethyl acetate (1 l). The organic layer was washed with saturated sodium bicarbonate solution, water and then saturated sodium chloride solution. The organic layer was dried over anhydrous magnesium sulfate and concentrated in vacuo.

The residue was separated and purified by a silica gel column chromatography to give two kinds of diastereomer of 2-[2-[(2S,4S)-3-acetyl-5,5-dimethyl-2-(2-methoxyphenyl)thiazolidine-4-ylcarbonyloxy]-5-methoxyphenyl]-3,4-dihydro-4-methyl-3-oxo-2H-1,4-benzothiazine-A (23.7 g, 50%) and -B (22.7 g, 48%), respectively.

diastereomer-A:
$[\alpha]_D^{25}-108.6°$ (c=1.0, chloroform.
IR: 1755, 1646, 1457, 1376, 1328, 1279, 1242, 1189, 1136, 1105.

diastereomer-B:
mp: 165°–166° C. (benzene—n-hexane).
$[\alpha]_D^{25}-108.3°$ (c=1.0, chloroform).
IR: 1756, 1653, 1457, 1373, 1331, 1280, 1244, 1192, 1139, 1106.

(ii) To a suspension of sodium borohydride (3.5 g) in anhydrous ethanol (80 ml), 2-[2-[(2S,4S)-3-acetyl-5,5-dimethyl-2-(2-methoxyphenyl)thiazolidine-4-ylcarbonyloxy]-5-methoxyphenyl]-3,4-dihydro-4-methyl-3-oxo-2H-1,4-benzothiazine-A (12.0 g), which was prepared by the process (i), dissolved in anhydrous tetrahydrofuran (40 ml) was added under ice-cooling. The mixture was stirred for 24 hours at the same temperature and concentrated in vacuo. To the residue, water (150 ml) was added and the product was extracted with ethyl acetate (250 ml). The organic layer was washed with saturated sodium chloride solution, dried over anhydrous magnesium sulfate and concentrated in vacuo. The oily residue was purified by the silica gel column chromatography to give 3.0 g (50%) of (−)-3,4-dihydro-2-(2-hydroxy-5-methoxyphenyl)-4-methyl-3-oxo-2H-1,4-benzothiazine.

mp 160.5°–161.5° C. (benzene—n-hexane).
$[\alpha]_D^{25}-30.6°$ (c=0.51, chloroform).
IR: 3224, 1625, 1582, 1429, 1366, 1264, 1218, 1201.

By the similar method, (+)-3,4-dihydro-2-(2-hydroxy-5-methoxyphenyl)-4-methyl-3-oxo-2H-1,4-benzothiazine was obtained from 2-[2-[(2S,4S)-3-acetyl-5,5-dimethyl-2-(2-methoxyphenyl)thiazolidine-4-ylcarbonyloxy]-5-methoxyphenyl]-3,4-dihydro-4-methyl-3-oxo-2H-1,4-benzothiazine-B.

mp 161.5°–162.5° C. (benzene—n-hexane).
$[\alpha]_D^{25}+31.8°$ (c=0.52, chloroform).

IR: 3220, 1625, 1582, 1429, 1366, 1264, 1218, 1201.

(iii) To a solution of (−)-3,4-dihydro-2-(2-hydroxy-5-methoxyphenyl)-4-methyl-3-oxo-2H-1,4-benzothiazine (6.3 g), which was prepared by the process (ii), in anhydrous tetrahydrofuran (70 ml), 3-bromo-1-propanol (8.8 g), triphenylphosphine (16.6 g) and then diethyl azodicarboxylate (10.0 ml) were added. The mixture was stirred for 2 hours under nitrogen atmosphere and concentrated in vacuo. The residue was purified by the silica gel column chromatography to give 4.5 g (51%) of (−)-3,4-dihydro-2-[2-(3-bromopropoxy)-5-methoxyphenyl]-4-methyl-3-oxo-2H-1,4-benzothiazine.

mp 77°–78° C. (ethanol).

$[\alpha]_D^{25} -195.9°$ (c=1.0, chloroform).

IR: 1643, 1584, 1491, 1464, 1359, 1271, 1239, 1201.

By the similar method, (+)-3,4-dihydro-2-[2-(3-bromopropoxy)-5-methoxyphenyl]-4-methyl-3-oxo-2H-1,4-benzothiazine was obtained from (+)-3,4-dihydro-2-(2-hydroxy-5-methoxyphenyl)-4-methyl-3-oxo-2H-1,4-benzothiazine.

mp 78°–79° C. (ethanol).

$[\alpha]_D^{25} +197.7°$ (c=1.0, chloroform).

IR: 1647, 1584, 1492, 1465, 1357, 1271, 1240, 1201.

(iv) Sodium iodide (4.3 g) was added to a solution of (−)-3,4-dihydro-2-[2-(3-bromopropoxy)-5-methoxyphenyl]-4-methyl-3-oxo-2H-1,4-benzothiazine (1.2 g), which was prepared by the process (iii), in acetone (30 ml). The mixture was refluxed for 12 hours and concentrated in vacuo. To the residue, water (30 ml) was added and the product was extracted with ethyl acetate (50 ml).

The organic layer was washed with saturated sodium chloride solution, dried over anhydrous magnesium sulfate, and concentrated in vacuo. To the residue dissolved in anhydrous dimethylformamide (20 ml), N-methyl-2-[(3,4-methylenedioxy)phenoxy]ethylamine (0.7 g) and triethylamine (0.3 g) were added and the mixture was stirred for 1.5 hours at 50° C. After cooling, water (50 ml) was added to the mixture and the product was extracted with ethyl acetate (80 ml). The organic layer was washed with saturated sodium chloride solution, dried over anhydrous magnesium sulfate, and concentrated in vacuo. To the residue fumaric acid (0.3 g) dissolved in ethanol (9 ml) was added. Precipitated crystals were collected by filtration to give 1.3 g (70%) of (−)-3,4-dihydro-2-[5-methoxy-2-[3-[N-methyl-N-[2-[(3,4-methylenedioxy]phenoxy]ethyl amino]-propoxy]phenyl]-4-methyl-3-oxo-2H-1,4-benzothiazine fumarate.

The physical data of the compound was identical with the compound prepared in Example 5.

By the similar method, (+)-3,4-dihydro-2-[5-methoxy-2-[3-[N-methyl-N-[2-[(3,4-methylenedioxy)-phenoxy]ethyl]amino]propoxy]phenyl]-4-methyl-3-oxo-2H-1,4-benzothiazine fumarate was obtained from (+)-3,4-dihydro-2-[2-(3-bromopropoxy)-5-methoxyphenyl]-4-methyl-3-oxo-2H-1,4-benzothiazine.

The physical data of the compound was identical with the compound prepared in Example 5.

The following compounds were prepared by the similar method as in Example 7.

(+)-3,4-dihydro-2-[5-methoxy-2-[4-[N-methyl-N-[2-[(3,4,5-trimethoxy)phenoxy]ethyl]amino]butoxy]-phenyl]-4-methyl-3-oxo-2H-1,4-benzothiazine fumarate (−)-3,4-dihydro-2-[5-methoxy-2-[4-[N-methyl-N-[2-[(3,4,5-trimethoxy)phenoxy]ethyl]amino]butoxy]-phenyl]-4-methyl-3-oxo-2H-1,4-benzothiazine fumarate (+)-3,4-dihydro-2-[5-methoxy-2-[4-[n-methyl-N-[2-[(3,4-methylenedioxy)phenoxy]ethyl]amino]butoxy]-phenyl]-4-methyl-3-oxo-2H-1,4-benzothiazine fumarate (−)-3,4-dihydro-2-[5-methoxy-2-[4-[N-methyl-N-[2-[(3,4-methylenedioxy)phenoxy]ethyl]amino]butoxy]-phenyl]-4-methyl-3-oxo-2H-1,4-benzothiazine fumarate The physical data of the compound was identical with the compound prepared in Example 5.

EXAMPLE 8

(examples of formulations)

As typical compounds of this invention, 3,4-dihydro-2-[5-methoxy-2-[4-[N-methyl-N-[2-[(3,4-methylenedioxy)phenoxy]ethyl]amino]butoxy]phenyl]-4-methyl-3-oxo-2H-1,4-benzothiazine oxalate (compound A) and 3,4-dihydro-2-[5-methoxy-2-[3-[N-methyl-N-[2-[(3,4-methylenedioxy)phenoxy]ethyl]amino]propoxy]-phenyl]-4-methyl-3-oxo-2H-1,4-benzothiazine fumarate were used.

(i) tablet

The following tablets were prepared by a direct compression of the compound A or B of this invention and excipients.

| compound A | 10 mg |
|---|---|
| crystalline cellulose | 48 mg |
| lactose | 35 mg |
| hydroxypropylcellulose-L | 4 mg |
| magnesium stearate | 3 mg |
| | 100 mg |
| compound B | 10 mg |
| crystalline cellulose | 48 mg |
| lactose | 35 mg |
| hydroxypropylcellulose-L | 4 mg |
| magnesium stearate | 3 mg |
| | 100 mg |

(ii) capsule

The following capsules were prepared using the compound A or B of this invention and lactose.

| compound A | 5 mg |
|---|---|
| lactose | 145 mg |
| | 150 mg |
| compound B | 5 mg |
| lactose | 145 mg |
| | 150 mg |

By changing the ratio of the compound A or B of this invention and lactose, capsules which contain the compound of this invention 10 mg, 30 mg, 50 mg, 100 mg in each capsule were prepared.

(iii) granule

The following granules were prepared by a usual method mixing the compound A or B of this invention, lactose and starch and using methanol solution of hydroxypropylcellulose-L as a binding agent.

|   |   |
|---|---|
| compound A | 50 mg |
| lactose | 55 mg |
| starch | 20 mg |
| hydroxypropylcellulose-L | 4 mg |
| talc | a little |
|   | 130 mg |

|   |   |
|---|---|
| compound B | 50 mg |
| lactose | 55 mg |
| starch | 20 mg |
| hydroxypropylcellulose-L | 4 mg |
| talc | a little |
|   | 130 mg |

The following coated granules were prepared as follows by a usual method. Granules were prepared first by a usual method mixing the compound A of this invention and mannitol and using aqueous polyvinylpyrrolidone K-30 solution as a binding agent and followed by coating with coating agent prepared by eudragid RL (trade name) and triacetine (plasticizer) by a usual method.

|   |   |
|---|---|
| compound A | 30 mg |
| mannitol | 46.5 mg |
| polyvinylpyrrolidone K-30 | 7 mg |
| eudragit RL | 15 mg |
| triacetine | 1.5 mg |
|   | 100 mg |

Granules of the compound B were prepared by the similar method.

|   |   |
|---|---|
| compound B | 30 mg |
| mannitol | 46.5 mg |
| polyvinylpyrrolidone K-30 | 7 mg |
| eudragit RL | 15 mg |
| triacetine | 1.5 mg |
|   | 100 mg |

What we claim is:

1. A compound or salts, wherein $R^1$ is hydrogen, lower alkyl, lower alkoxy, halogen or nitro.

2. The compound or salts thereof as in claim 1, wherein $R^3$ is hydrogen, lower alkyl, lower alkoxy, halogen, lower alkyelendioxy or

3. The compound or salts thereof as in claim 1, wherein $R^1$ is lower alkoxy, $R^2$ is lower alkyl, $R^3$ is lower alkylenedioxy and $R^4$ is lower alkyl.

4. The compound or salts thereof as in claim 1, wherein the compound is an optically active compound.

5. 3,4-Dihydro-2-[5-methoxy-2-[3-[N-methyl-N-[2-[(3,4-methylenedioxy)phenoxy]ethyl]amino]propoxy]-phenyl]-4-methyl-3-oxo-2H-1,4-benzothiazine or salts thereof.

6. 3,4-Dihydro-2-[5-methoxy-2-[4-[N-metyl-N-[2-[(3,4-methylenedioxy)phenoxy]ethyl]amino]butoxy]-phenyl]-4-methyl-3-oxo-2H-1,4-benzothiazine or salts thereof.

7. 3,4-Dihydro-2-[5-methoxy-2-[4-[N-methyl-N-[2-[(3,4-dimethoxy)phenoxy]ethyl]amino]butoxy]phenyl]-4-methyl-3-oxo-2H-1,4-benzothiazine or salts thereof.

8. The compound as in claim 5, wherein the compound is an optically active compound.

9. A compound of the formula (I) or a salt thereof,

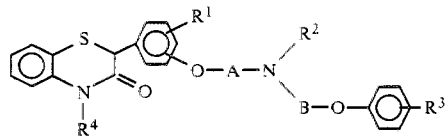

wherein $R^1$ is one or more groups selected from those consisting of hydrogen, lower alkyl, halogen, nitro, hydroxy, lower alkoxy, lower alkanoyloxy, amino, lower alkylamino and lower alkoxycarbonyloxy;

$R^2$ is hydrogen, lower alkyl or $(C_3-C_6)$cycloalkyl;

$R^3$ is one or more groups selected from those consisting of hydrogen, lower alkyl, hydroxy, lower alkoxy, halogen, nitro, lower alkylenedioxy wherein the oxygens are on adjacent positions, lower alkanoyloxy, lower alkanoyl, amino, lower alkylamino, lower alkanoylamino and lower alkoxycarbonyloxy or

$R^4$ is hydrogen or lower alkyl;

A and B are same or different and are lower alkylene having 1 to 6 carbon atoms; and n is 3 to 4.

10. A pharmaceutical composition comprising (i) a pharmaceutical carrier and (ii) a platelet anti-aggregative effective amount of a compound of the formula (I):

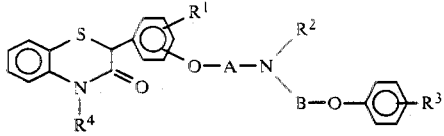

wherein $R^1$ is one or more groups selected from those consisting of hydrogen, lower alkyl, halogen, nitro, hydroxy, lower alkoxy, lower alkanoyloxy, amino, lower alkylamino and lower alkoxycarbonylox;

$R^2$ is hydrogen, lower alkyl or $(C_3-C_6)$cycloalkyl;

$R^3$ is one or more groups selected from those consisting of hydrogen, lower alkyl, hydroxy, lower alkoxy, halogen, nitro, lower alkylenedioxy wherein the oxygens are on adjacent positions, lower alkanoyloxy, lower alkanoyl, amino, lower alkylamino, lower alkanoylamino and lower alkoxycarbonyloxy or

$R^4$ is hydrogen or lower alkyl;

A and B are same or different and are lower alkylene having 1 to 6 carbon atoms; and n is 3 to 4.

11. The compound or salt thereof of claim 9 wherein each lower alkyl is individually selected from the group consisting of methyl, ethyl, propyl and hexyl; each halogen is individually selected from the group consisting of fluorine, chlorine and bromine; each lower alkoxy is individually selected from the group consisting of methoxy, ethoxy, propoxy and hexyloxy; each lower alkanoyloxy is individually selected from the group consisting of acetyloxy, propionyloxy and hexanoyloxy; each (C-C) cycloalkyl is individually selected from the group consisting of cyclopropyl and cyclohexyl; each lower alkylenedioxy is selected from the group consisting of methylenedioxy and ethylenedioxy; and each lower alkanoyl is selected from the group consisting of acetyl, propionyl and hexanoyl.

12. The compound or salt thereof of claim 9 wherein
$R^1$ is methoxy or hydrogen;
$R_2$ is hydrogen, methyl, ethyl, cyclopropyl or cyclohexyl;
$R_4$ is methyl or hydrogen;
A is methylene; and
B is methylene.

13. The compound of claim 12 wherein each $R_3$ is methoxy.

14. The compound of claim 12 wherein $R_3$ is methylenedioxy.

15. The compound of claim 12 wherein $R_3$ is chlorine or fluorine.

16. The compound of claim 12 wherein $R_3$ is $NO_2$.

17. A pharmaceutical composition comprising (i) a pharmaceutical carrier and (ii) a calcium antagonistic effective amount of a compound of the formula (I):

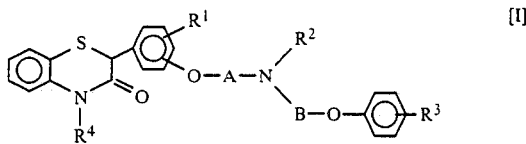

wherein
$R^1$ is one or more groups selected from those consisting of hydrogen, lower alkyl, halogen, nitro, hydroxy, lower alkoxy, lower alkanoyloxy, amino, lower alkylamino and lower alkoxycarbonyloxy;
$R^2$ is hydrogen, lower alkyl or $(C_3-C_6)$ cycloalkyl;
$R^3$ is one or more groups selected from those consisting of hydrogen, lower alkyl, hydroxy, lower alkoxy, halogen, nitro, lower alkylenedioxy wherein the oxygens are on adjacent positions, lower alkanoyloxy, lower alkanoyl, amino, lower alkylamino, lower alkanoylamino and lower alkoxycarbonyloxy or

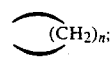

$R^4$ is hydrogen or lower alkyl;
A and B are same or different and are lower alkylene having 1 to 6 carbon atoms; and
n is 3 to 4.

* * * * *